United States Patent
Wei et al.

(10) Patent No.: US 11,226,318 B2
(45) Date of Patent: Jan. 18, 2022

(54) METHOD FOR HIGH-THROUGHPUT SCREENING OF NON-TARGET BIOMARKERS BASED ON METABOLIC PERTURBATION CAUSED BY POLLUTANTS

(71) Applicant: NANJING UNIVERSITY, Nanjing (CN)

(72) Inventors: Si Wei, Nanjing (CN); Yuqian Li, Nanjing (CN); Hongxia Yu, Nanjing (CN); Nanyang Yu, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 0 days.

(21) Appl. No.: 17/050,455

(22) PCT Filed: May 18, 2020

(86) PCT No.: PCT/CN2020/090832
§ 371 (c)(1),
(2) Date: Oct. 26, 2020

(87) PCT Pub. No.: WO2021/217745
PCT Pub. Date: Nov. 4, 2021

(65) Prior Publication Data
US 2021/0333250 A1 Oct. 28, 2021

(30) Foreign Application Priority Data
Apr. 26, 2020 (CN) .......................... 202010338854.6

(51) Int. Cl.
*G01N 30/86* (2006.01)
*G16B 5/00* (2019.01)
(Continued)

(52) U.S. Cl.
CPC ......... *G01N 30/8631* (2013.01); *G01N 30/06* (2013.01); *G01N 30/7233* (2013.01);
(Continued)

(58) Field of Classification Search
None
See application file for complete search history.

(56) References Cited

FOREIGN PATENT DOCUMENTS

| CN | 104101674 A | 10/2014 |
| CN | 105891365 A | 8/2016 |

(Continued)

OTHER PUBLICATIONS

Plabmann, Merle, et al., human-biomonitoring of new contaminants: Sub-project 2-Screening of target and non-target contaminants in human blood and urine Environmental Research of the Federal Ministry for the Environment., Nature Conservation and Nuclear Safety, Project No. (FKZ) 371062202, May 31, 2014.

*Primary Examiner* — Daniel S Larkin
(74) *Attorney, Agent, or Firm* — Zhihua Han; WEN IP LLC

(57) ABSTRACT

Disclosed is a method for high-throughput screening of non-target biomarkers based on metabolic disturbance caused by pollutants, belonging to the field of environmental exposure and health. The method includes the following steps: (1) extracting to obtain extracts to be tested; (2) performing chromatographic analysis to obtain a spectrum containing chromatographic peaks; (3) identifying and labeling features of pollutants, taking chromatographic peaks other than the features of the pollutants as features of potential metabolites, and performing non-target labeling of the features of the potential metabolites; (4) establishing a linear regression model by taking the peak areas of the features of the potential metabolites as dependent variables and the peak areas of the features of the pollutants as independent variables; (5) operating the model, and performing non-target screening of the biomarkers to preliminarily obtain related biomarkers; (6) identifying the MS spectra and MS/MS spectra of the preliminarily obtained biomarkers, and identifying biomarkers related to pollutant (Continued)

exposure. The disclosed method improves the accuracy of biomarker screening and the throughput of biomarker screening.

11 Claims, 5 Drawing Sheets

(51) Int. Cl.
  *G01N 30/72* (2006.01)
  *G01N 30/06* (2006.01)
  G01N 30/02 (2006.01)

(52) U.S. Cl.
  CPC ......... *G16B 5/00* (2019.02); *G01N 2030/027* (2013.01); *G01N 2030/062* (2013.01)

(56) References Cited

FOREIGN PATENT DOCUMENTS

| | | |
|---|---|---|
| CN | 106018600 A | 10/2016 |
| CN | 107179366 A | 9/2017 |
| CN | 109187840 A | 1/2019 |
| CN | 109668984 A | 4/2019 |

METHOD FOR HIGH-THROUGHPUT SCREENING OF NON-TARGET BIOMARKERS BASED ON METABOLIC PERTURBATION CAUSED BY POLLUTANTS

TECHNICAL FIELD

The present invention belongs to the field of environmental exposure and health, and particularly involves a method for high-throughput screening of non-target biomarkers based on a metabolic disturbance caused by pollutants.

BACKGROUND

With the development of science and technology and the improvement of people's living standards, pollutants generated are also increasing. These substances are released and accumulated in the environment. Organisms are exposed to various environmental media, and pollutants in the environment may enter the organisms through various ways such as touching, breathing, eating, etc, resulting in the transformation from external exposure to internal exposure. Exogenous environmental pollutants entering organisms cause a potential threat to organisms, and plenty of evidence indicate that exposure to specific chemicals may lead to diseases.

Biomarkers are indicators of abnormal changes observed before the organisms are subjected to severe toxicity. At present, the omics technologies of biomarkers include genomics, proteomics, metabolomics, etc. The metabolomics is a qualitative and quantitative study of metabolites with low molecular mass, which is considered to be the closest omics to phenotype. The metabolomics has been developed rapidly in recent years, but the related research still lags behind the genomics and the proteomics. Research on the metabolomic disturbance caused by environmental pollutants can fill this gap, so as to realize the prediction of toxicity and contribute to scientific control of pollutants.

The problems of current metabolomics research are as follows: on the one hand, the screening throughput is insufficient, and most of the research is targeted research, which leads to the biomarkers that are not in the scope of research are easily ignored, thus affecting the accuracy of screening; on the other hand, because of the complexity of environmental pollutants and metabolites of organisms, it is difficult to study the correlation of metabolomics, and statistical tools need to be optimized.

In view of the defects of the prior art, it is urgent to develop a screening method for metabolomic biomarkers with high throughput and high accuracy.

SUMMARY

1. Problems to be Solved

In view of the problems of insufficient screening throughput and low accuracy in the research of metabolomics in the prior art, a screening method of the present invention is provided. First, non-target screening of potential metabolites is performed, and then the range is gradually reduced to obtain a small number of biomarkers, which can ensure more comprehensive screening, and realize high-throughput and accurate screening and identification of biomarkers, so as to provide the scientific basis for toxicity prediction and pollutant risk assessment and control.

2. Technical Solutions

In order to solve the foregoing problems, the technical solutions adopted by the present invention are as follows:

A method for high-throughput screening of non-target biomarkers based on a metabolic disturbance caused by pollutants according to the present invention includes the following steps:

(1) sample extraction: performing sample treatment, and extracting pollutants and metabolites from biological samples to obtain extracts to be tested;

(2) chromatographic analysis: performing full scan analysis and detection of the extracts to be tested through a high performance liquid chromatography—time-of-flight mass spectrometer to obtain a spectrum containing chromatographic peaks;

(3) pollutant labeling and non-target labeling of potential metabolites: identifying and labeling features of pollutants according to the spectrum, taking features other than the features of the pollutants as features of the potential metabolites, and performing non-target labeling of the features of the potential metabolites;

(4) establishment of model: establishing a linear regression model by taking the peak areas of the features of the potential metabolites as dependent variables and the peak areas of the features of the pollutants as independent variables;

(5) non-target screening of biomarkers: operating the model to perform non-target screening of the biomarkers, obtaining related biomarkers by preliminary screening; and (6) identification of biomarkers: identifying the MS spectra and MS/MS spectra of the biomarkers obtained in step (5), and identifying biomarkers related to pollutant exposure.

Preferably, the method further includes step (7): using correction method to correct the model, operating the corrected model, and repeating steps (5)-(6).

Preferably, the method further includes the step of metabolic pathway enrichment of the biomarkers; in this step, the identified biomarkers are enriched into metabolic pathways to obtain the metabolic pathways disturbed by pollutants.

Preferably, the correction method includes false discovery rate (FDR) correction and interference factor correction; in the process of the FDR correction, threshold $p<0.05$ is corrected to be FDR<20%; and in the process of the interference factor correction, interference factors existing in samples are added to the model as covariates for correction.

Preferably, when the extracts to-be-tested contain multiple pollutants, the correction method includes a co-exposure correction method: taking multiple pollutants as potential independent variables to perform multiple stepwise regression and model correction.

Preferably, in the process of identifying the features of the pollutants, the spectrum is converted into a WIFF file, i.e., an AB SCIEX Windows Interchange File Format data file, and the peaks in the WIFF file, an AB SCIEX Windows Interchange File Format data file, are imported into PEAKVIEW® Software, a Mass Spec data interrogation software and aligned to identify the pollutants.

Preferably, in the process of non-target labeling of the features of the potential metabolites, the spectrum is converted into an ABF file, wherein ABF file is a backup file created by Analysis Services, a component of Microsoft SQL Server used for online analytical processing (OLAP) and data mining. The peaks in the ABF file are imported into MSDIAL software and aligned, and then the features with detection rate greater than 80% are retained as the features of the potential metabolites. The MSDIAL software is a universal software program for untargeted metabolomics that supports multiple mass spectrometry (MS) instruments (e.g., gas chromatography-mass spectrometry (GC/MS) and liquid chromatography-mass spectrometry (LC/MS)) and MS vendors.

Preferably, in step (4), the model with significance p<0.05 after operation is taken as an effective model to implement the operation process of step (5).

Preferably, in step (6), MSDIAL software, a universal software program for untargeted metabolomics that supports multiple MS instruments and MS vendors, and MetDNA platform, an internet-based platform with URL of http://metdna.zhulab.cn/ that implements a metabolic reaction network (MRN) based recursive algorithm for metabolite identification and supports data from different LC systems and MS platforms, are combined to identify the biomarkers.

Preferably, after step (4), the method further includes the prediction of a metabolic disturbance: pollutant molecules with identified structures are subjected to structural optimization in SYBYL® software, a molecular modeling program for creating molecular model from sequence through lead optimization and has capabilities for small molecule modeling and simulation, macromolecular modeling and simulation, and cheminformatics and lead identification. Tripos force field, Gasteiger-Huckel charge and a Powell gradient method are applied until the termination gradient drops below 0.001 kcal/(mol·Å). In addition, the protein structure is downloaded from the protein database (http://www.rcsb.org), then the ligand is extracted from the SYBYL® software, a molecular modeling program for creating molecular model from sequence through lead optimization and has capabilities for small molecule modeling and simulation, macromolecular modeling and simulation, and cheminformatics and lead identification, to form a docking pocket, the crystal water is removed, and protonated. The optimized ligand of the pollutant and the protein pocket are docked in the SYBYL® software, a molecular modeling program for creating molecular model from sequence through lead optimization and has capabilities for small molecule modeling and simulation, macromolecular modeling and simulation, and cheminformatics and lead identification, and the optimum conformation is selected as docking result. The greater the total score of the docking result, the stronger the docking ability, and the less free pollutants; otherwise, free pollutants are more, which may lead to stronger transient metabolic disorder and more biomarkers. This step is to select pollutants for preferential prediction when a large number of pollutants are studied.

Preferably, the specific steps of the method are as follows:

(1) sample extraction: solid samples (such as biological tissues) are homogenized. Liquid samples (such as blood and urine) are placed in a centrifuge tube, and 0.26-0.28 g of magnesium sulfate-sodium chloride mixture and acetonitrile are added into the samples and then the samples are swirled immediately, at this time, the samples are in suspension; ultrasonic extraction of the samples is performed for 30 min and centrifugated, then the supernatant is transferred. The residue is extracted twice with 95% acetonitrile-aqueous solution, and the extracts are combined. The extracts are blown with nitrogen to be nearly dry, transferred to a chromatographic sample bottle and made up to volume with acetonitrile. If a small amount of white solid exists at the bottom, additional centrifugation is performed and the supernatant is transferred to the chromatographic sample bottle.

The pretreatment method according to the present invention reduces the pre-filtration of metabolites in the samples, and subsequently biomarkers can be screened in a more comprehensive range.

(2) Instrument analysis: the extracted samples are subjected to full scan analysis and detection through a high performance liquid chromatography—time-of-flight mass spectrometer. Parameters are as follows:

high performance liquid chromatographic instrument: Infinity1260;

chromatographic column: C18 column: (2.1 mm×50 mm, 2.5 μm);

column temperature: 40° C.;

flow rate: 0.4 mL/min;

mobile phase: 0.1% formic acid-aqueous solution (phase A in positive ion mode), 2 mM ammonium acetate aqueous solution (phase A in negative ion mode) and methanol (phase B); and Table 1 shows the gradient elution conditions.

TABLE 1

Gradient elution conditions

| Time (min) | A % | B % |
|---|---|---|
| 1.00 | 95 | 5 |
| 11.00 | 75 | 25 |
| 19.00 | 50 | 50 |
| 25.00 | 25 | 75 |
| 29.00 | 0 | 100 |
| 32.00 | 0 | 100 |
| 32.01 | 95 | 5 |
| 36.00 | 100 | 0 | mass spectrometer instrument: Triple TOF 4600;

full scan mode: data dependence mode;

ion source: positive and negative electrospray ionization source;

full scan mass range: MS 50-1250 Da, MS/MS 30-1000 Da;

collision energy: ±40 eV;

collision energy spread: 20 eV;

ion source temperature: 550° C.

(3) Labeling and identification of features of pollutants: the spectrum obtained after instrumental analysis is converted into a WIFF file, an AB SCIEX Windows Interchange File Format data file, the peaks in the WIFF file are imported into PEAKVIEW® Software, a Mass Spec data interrogation software and aligned for analysis, and pollutants with standard samples are identified by matching retention time and mass spectrum fragments. The structure of pollutants without standard samples can be calculated by analyzing the fragments of mass spectra using Formula Finder function.

Parameters are as follows:

peak picking mass range: 50-1250 Da;

peak picking mass error: 0.01 Da;

alignment retention time error: 2 min;

alignment mass error: 0.01 Da;

identification mass error: MS 0.01 Da, MS/MS 0.005 Da.

(4) Non-target labeling of characteristic peaks of metabolites: the spectrum obtained after instrumental analysis are converted into an ABF file, a backup file created by Analysis Services, a component of Microsoft SQL Server used for online analytical processing (OLAP) and data mining. The peaks in the ABF file are imported into MSDIAL software, a universal software program for untargeted metabolomics that supports multiple MS instruments and MS vendors, and aligned. Features with detection rate greater than 80% other than the features of the pollutants are taken as features of potential metabolites, and the peak area and mass spectrum corresponding to each peak are subjected to statistical processing and listed as a chromatographic peak table. Parameters are as follows:

Peak picking mass range: 30-1250 Da;
Peak picking mass error: 0.01 Da;
alignment retention time error: 0.5 min;
alignment mass error: 0.015 Da.

(5) Non-target screening of biomarkers: a linear regression model is established in SPSS® software a software package used for interactive, or batched, statistical analysis, the dependent variables are the peak areas of the features of the potential metabolites subjected to non-target labeling in (4), the independent variables are the peak areas of the features of the pollutants in (3), the model with significance $p<0.05$ after operation is regarded as an effective model, the non-target screening of biomarkers is performed to obtain related biomarkers by preliminary screening.

(6) High-throughput identification of biomarkers: the MS spectra and MS/MS spectra of the related biomarker features obtained by preliminary screening in step (5) are subjected to programmed identification by multi-platform combination.

Firstly, MSP (a file extension associated with Windows Installer Patch file used for updating Windows and Microsoft programs) files in positive and negative ion modes are loaded in MSDIAL software, a universal software program for untargeted metabolomics that supports multiple MS instruments and MS vendors, respectively for metabolite library alignment. Unmatched metabolic features are uploaded to MetDNA platform (an internet-based platform with URL at http://metdna.zhulab.cn/ that implements a metabolic reaction network (MRN) based recursive algorithm for metabolite identification and supports data from different LC systems and MS platforms), for further identification. Identification results are classified in confidence level according to the standard recommended by Metabolites Standards Initiative (MSI): the metabolites identified by MSDIAL, a universal software program for untargeted metabolomics that supports multiple MS instruments and MS vendors, are at level 2; the "seed" metabolites identified by MetDNA are level 2, and other metabolites identified by MetDNA are at level 3, wherein MetDNA is an internet-based platform with URL at http://metdna.zhulab.cn/ that implements a metabolic reaction network (MRN) based recursive algorithm for metabolite identification and supports data from different LC systems and MS platforms. MSDIAL (a universal software program for untargeted metabolomics that supports multiple MS instruments and MS vendors) parameters are as follows:

mass error: MS 0.01 Da, MS/MS 0.05 Da.
threshold of score: 80 points.

(7) Model correction: a linear regression model is established through multiple corrections to reduce false positive results. The correction method includes:

false discovery rate (FDR) correction: using R software to correct the threshold $p<0.05$ to FDR<20% through a qvalue command;

interference factor correction: adding interference factors existing in samples to the regression model as covariates; and co-exposure correction: when multiple pollutants are studied simultaneously, taking multiple pollutants as potential independent variables for multiple stepwise regression. Specifically, when a model of a pollutant is analyzed, a multiple regression model is operated by taking biomarkers as dependent variables and other pollutants as independent variables, and a "stepwise" method is selected to retain significant pollutants as final independent variables and delete non-significant pollutants.

After operation of the model, the regression model of the following three objects is obtained: ①  dependent variable: biomarker; ② independent variable 1: a specific pollutant analyzed; ③ independent variable 2: significant pollutants the among other pollutants. In this case, the significance of item ② (independent variable 1: a pollutant analyzed) is the significance P value after correction, and the metabolite with the p-value still less than 0.05 is used as the final biomarker corresponding to this specific pollutant, and the process of biomarker high-throughput identification in step (6) is repeated.

(8) Metabolic pathway enrichment of the biomarkers: the biomarkers are enriched into metabolic pathways to obtain metabolic pathways disturbed by pollutants.

3. Beneficial Effects

Compared with the prior art, the present invention has the following beneficial effects:

(1) In the method for high-throughput screening of non-target biomarkers based on a metabolic disturbance caused by pollutants according to the present invention, on the basis of the chromatograms obtained by detection, the features of pollutants are identified, then other chromatographic peaks with high detection rate other than the features of the pollutants are taken as potential metabolites, and non-target labeling is performed on them. By establishment of a linear regression model between pollutants and potential metabolites, preliminary screening results of biomarkers related to pollutant exposure are obtained, and then through structural identification of the preliminarily screened biomarkers, fewer and more accurate biomarkers with higher correlation with pollutant exposure are identified and enriched into metabolic pathways, so that metabolic pathways disturbed by pollutant metabolism can be obtained. The method of the present invention starts with the analysis of all chromatographic peaks obtained by detection, and gradual screening is performed to narrow the range, and finally screening results with higher accuracy are obtained. It is not only suitable for high-throughput pollutant screening, but also has higher accuracy.

(2) In the method for high-throughput screening of non-target biomarkers based on a metabolic disturbance caused by pollutants according to the present invention, firstly, non-target screening of potential metabolites is performed, and then the range is gradually narrowed to obtain a small number of biomarkers. This can effectively overcome the defect that complete identification cannot be ensured when using targeted screening for biomarkers. The method of the present invention can ensure more comprehensive screening to obtain more accurate biomarker information, which can reflect the strength of the metabolic disturbance caused by pollutants.

(3) In the method for high-throughput screening of non-target biomarkers based on a metabolic disturbance caused by pollutants according to the present invention, MSDIAL software, a universal software program for untargeted metabolomics that supports multiple MS instruments and MS vendors, and MetDNA platform, an internet-based platform with URL at http://metdna.zhulab.cn/that implements a metabolic reaction network (MRN) based recursive algorithm for metabolite identification and supports data from different LC systems and MS platforms, are combined to identify screened biomarkers, improving the identification efficiency and increasing the throughput of the identified biomarkers.

(4) According to the present invention, the statistical analysis model is corrected in a mode of co-exposure correction, so that under the conditions of co-exposure of various pollutants, the disturbance of other pollutants can be eliminated and biomarkers of a specific pollutant can be accurately screened, which making the model analysis results more accurate, and the actual exposure can be analyzed more reasonably. Therefore, the false positive is reduced and the accuracy of results is improved.

DETAILED DESCRIPTION

The present invention is further described below with reference to specific examples.

Example 1

This example relates to a method for high-throughput screening of non-target biomarkers based on a metabolic disturbance caused by perfluorinated pollutants in the blood medium. The method includes the following steps:

(1) 0.5 mL of serum sample is placed into a 15 mL centrifuge tube, 0.26-0.28 g of magnesium sulfate-sodium chloride mixture and 1.5 mL of acetonitrile are added, and then the sample is swirled immediately. At this time, the sample is in suspension. Ultrasonic extraction of the sample is performed for 30 min and centrifugated, then the supernatant is transferred. The residue is extracted twice with 95% acetonitrile-aqueous solution, and the extracts are combined. The extracts are blown with nitrogen to be nearly dry, transferred to a chromatographic sample bottle and made up to 100 μL with acetonitrile.

(2) Instrument analysis: the extracted samples are subjected to full scan analysis and detection through a high-performance liquid chromatography—time-of-flight mass spectrometer. Parameters are as follows:

high performance liquid chromatographic instrument: Infinity 1260;

chromatographic column: C18 column: (2.1 mm×50 mm, 2.5 μm);

column temperature: 40° C.;

flow rate: 0.4 mL/min;

mobile phase: 0.1% formic acid-aqueous solution (phase A in positive ion mode), 2 mM ammonium acetate aqueous solution (phase A in negative ion mode) and methanol (phase B).

Table 2 shows the gradient elution conditions.

TABLE 2

Gradient elution conditions

| time (min) | A % | B % |
|---|---|---|
| 1.00 | 95 | 5 |
| 11.00 | 75 | 25 |
| 19.00 | 50 | 50 |
| 25.00 | 25 | 75 |
| 29.00 | 0 | 100 |
| 32.00 | 0 | 100 |
| 32.01 | 95 | 5 |
| 36.00 | 100 | 0 | mass spectrometer instrument: Triple TOF 4600;

full scan mode: data dependence mode;

ion source: positive and negative electrospray ionization source;

full scan mass range: MS 50-1250 Da, MS/MS 30-1000 Da;

collision energy: ±40 eV;

collision energy spread: 20 eV;

ion source temperature: 550° C.

Figure 1:
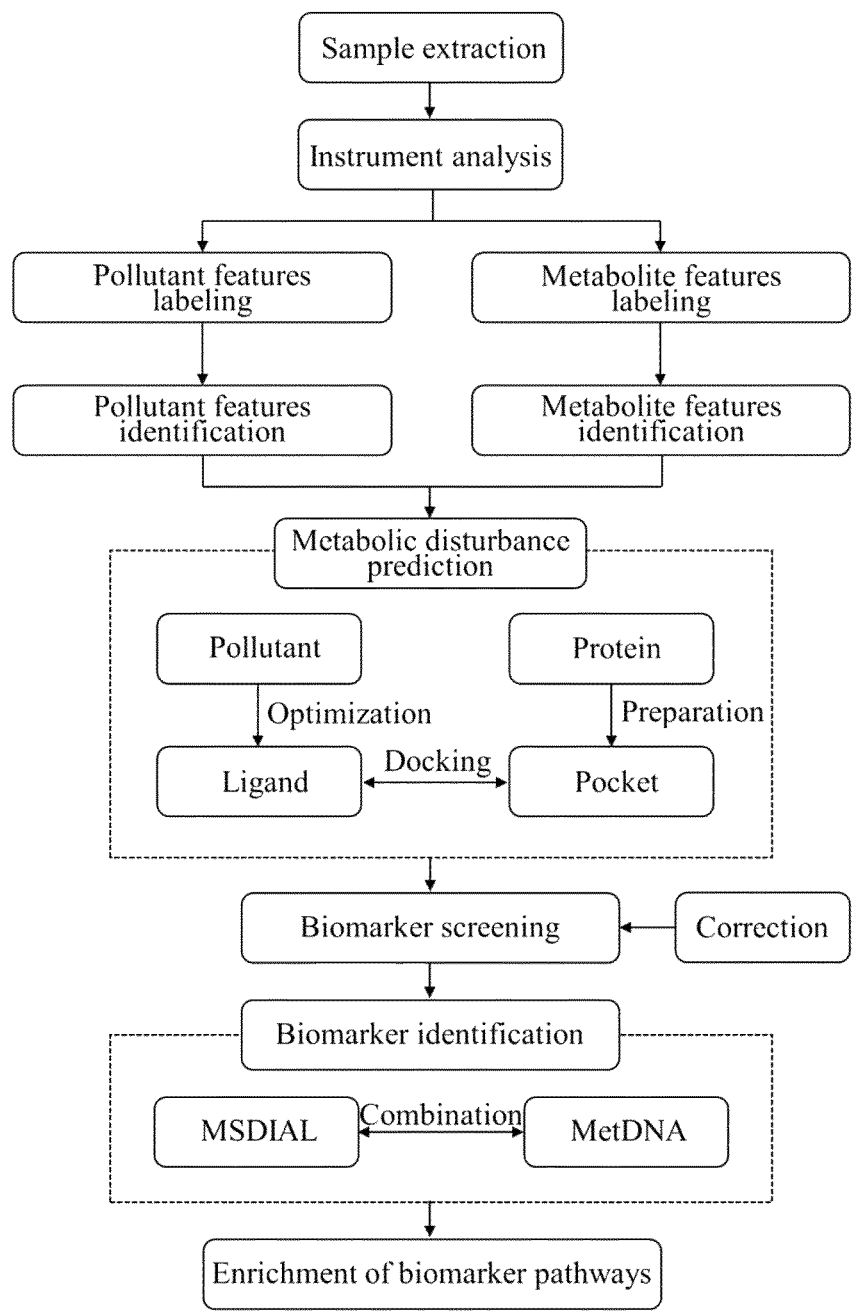
FIG. 1 is a flowchart of a method for non-target screening of biomarkers in Example 1.
Figure 2:
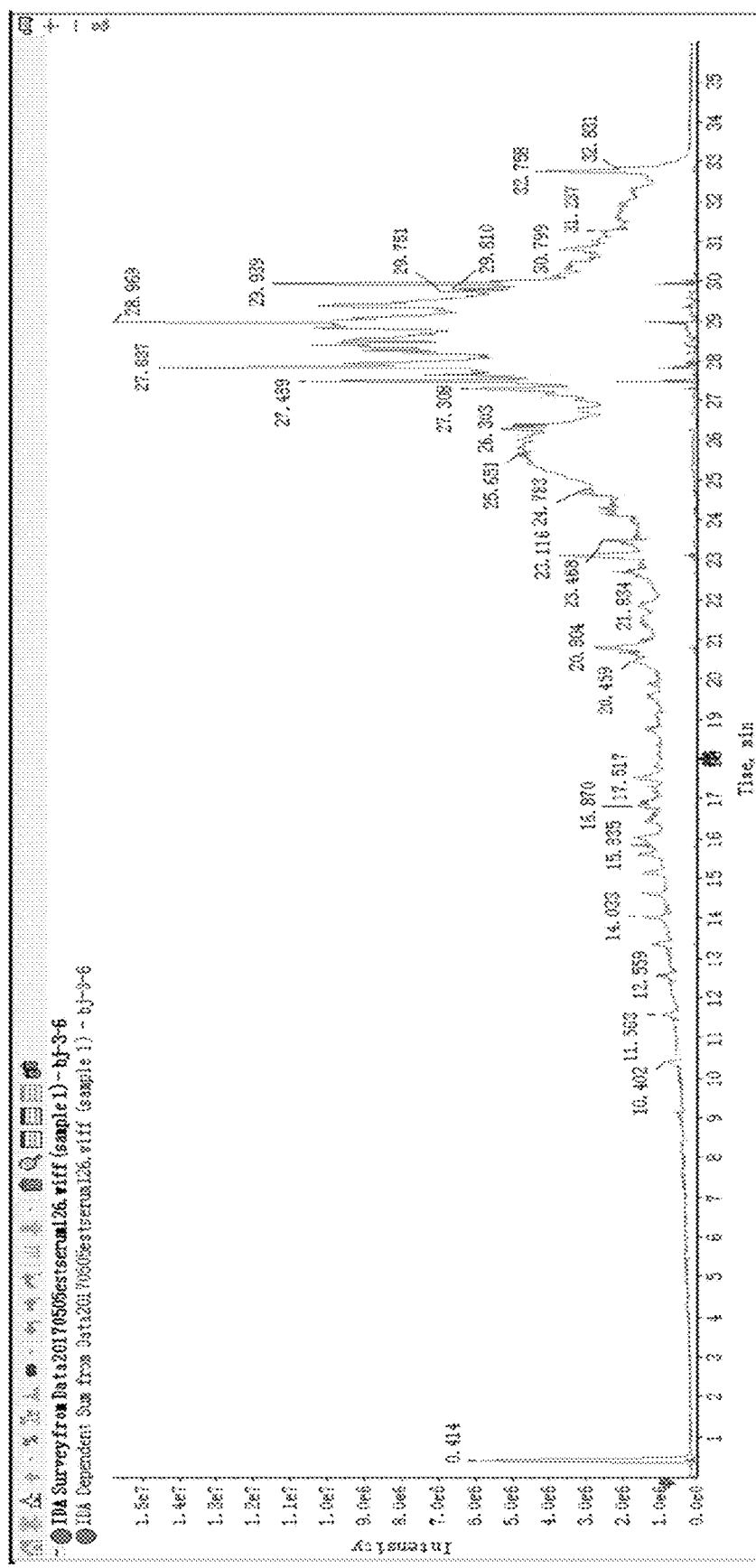
FIG. 2 is the chromatogram obtained from sample analysis in Example 1.
Figure 3:
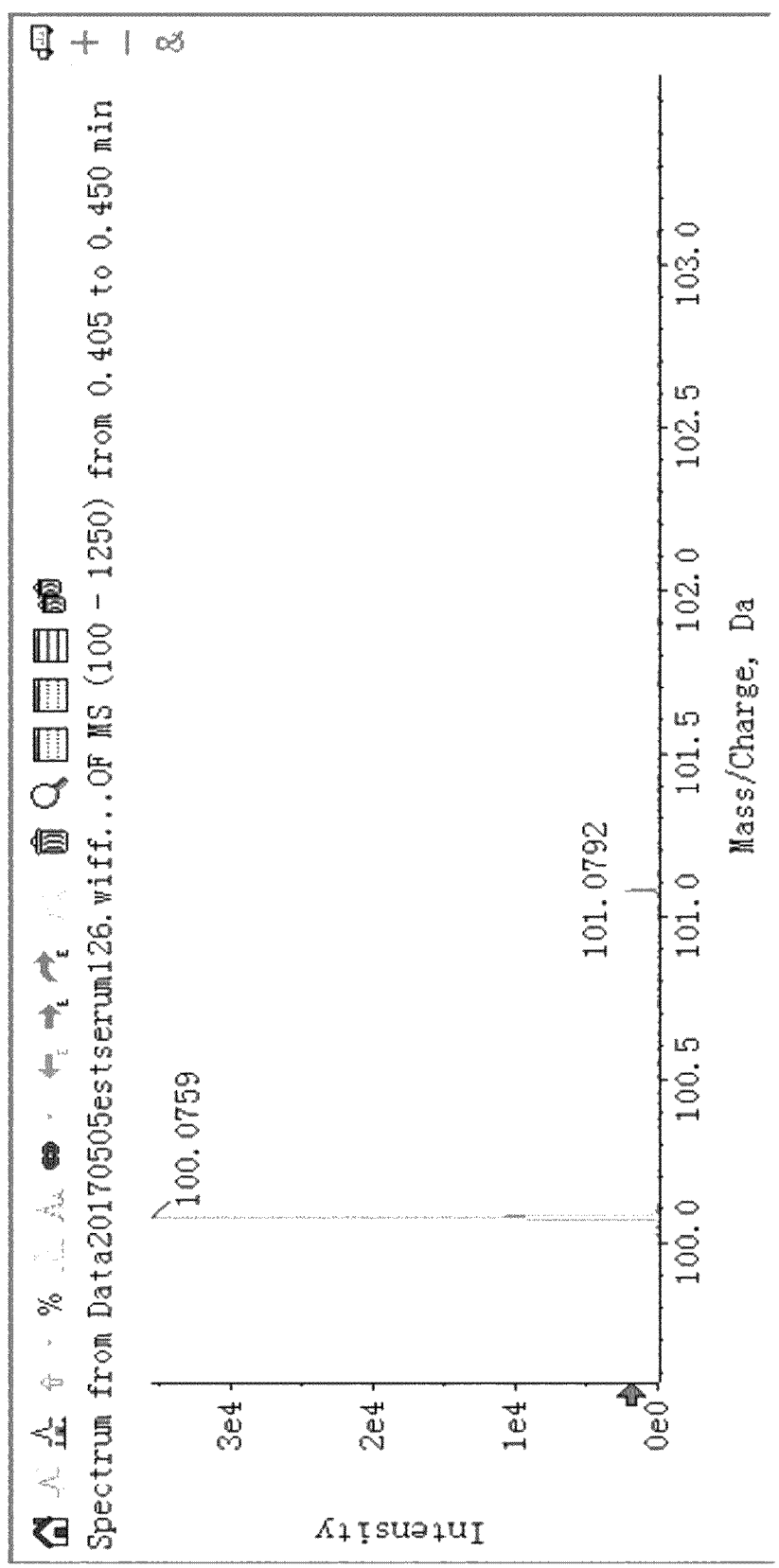
FIG. 3 is the MS spectrum obtained from sample analysis in Example 1.
Figure 4:
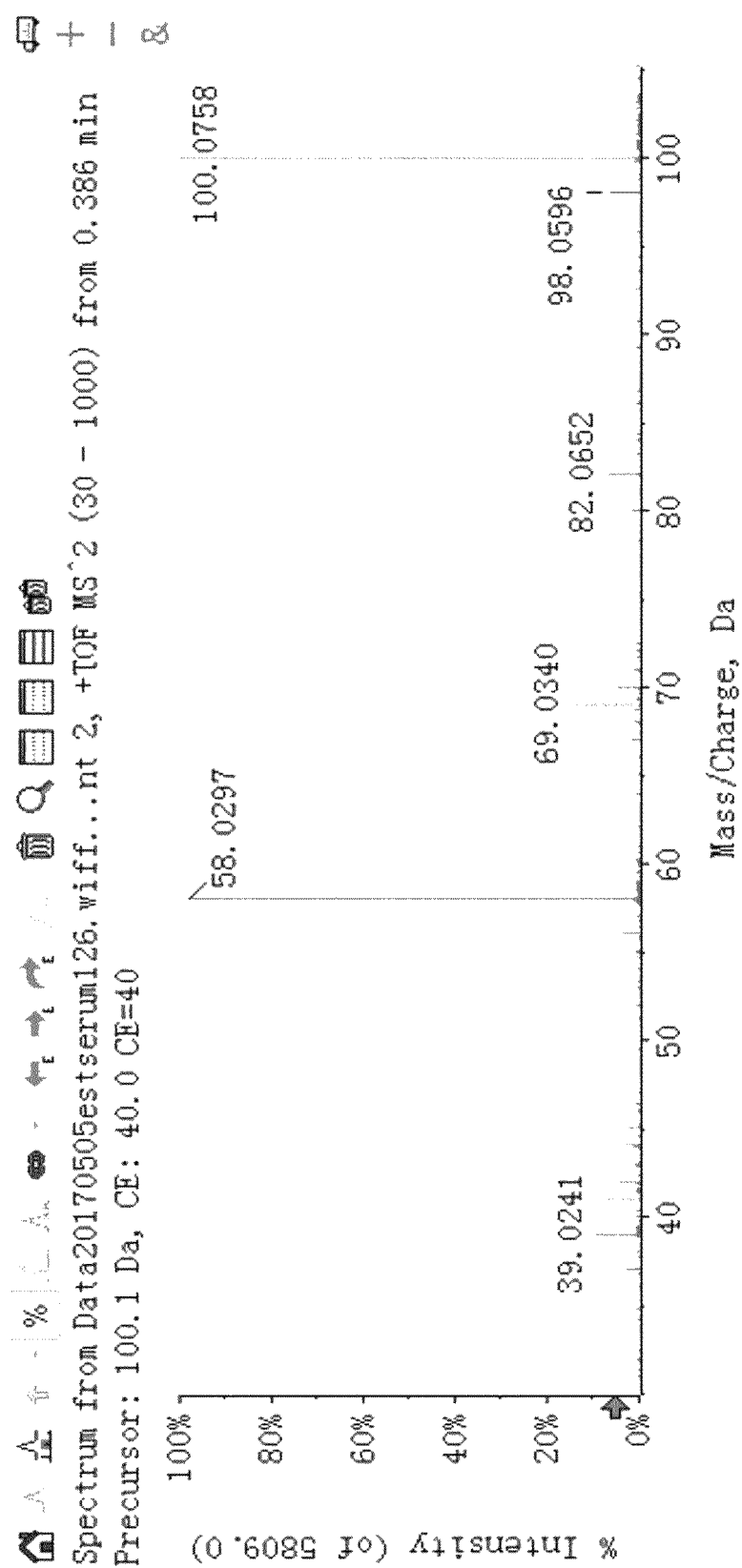
FIG. 4 is the MS/MS spectrum obtained from sample analysis in Example 1.

(3) Labeling and identification of features of pollutants: the spectrum obtained after instrumental analysis is converted into a WIFF file, an AB SCIEX Windows Interchange File Format data file, the peaks in the WIFF file are imported into PEAKVIEW® Software, a Mass Spec data interrogation software and aligned for analysis. The chromatogram of the sample is obtained, as shown in FIG. 2. A specific chromatographic peak is selected, and the MS spectrum and the MS/MS spectrum of the substance can be obtained, the MS spectrum is shown in FIG. 3 and the MS/MS spectrum is shown in FIG. 4.

The pollutants of interest in this example are perfluorinated compounds, which are novel pollutants widely existing in the environment and organisms. Legacy perfluorocarboxylic acid and perfluorosulfonic acid are identified by matching retention time and mass spectrum fragments with those of standard samples. The structure of the novel perfluorinated substances without standard samples can be calculated by analyzing the fragments of mass spectra using Formula Finder function. Parameters are as follows:

peak picking mass range: 50-1250 Da;

peak picking mass error: 0.01 Da;

alignment retention time error: 2 min;

alignment mass error: 0.01 Da;

identification mass error: MS 0.01 Da, MS/MS 0.005 Da.

The perfluorinated pollutants identified by the above steps are shown in Table 3.

TABLE 3

Identified perfluorinated pollutants

| Name | Abbreviation | Mass number (Da) | Retention time (min) |
|---|---|---|---|
| Perfluorooctanoate | PFOA | 412.9664 | 19.94 |
| Perfluorononanoate | PFNA | 462.9632 | 21.35 |
| Perfluorodecanoate | PFDA | 512.9600 | 22.54 |
| Perfluoroundecanoate | PFUnDA | 562.9568 | 23.63 |
| Perfluorohexanesulfonate | PFHxS | 398.9366 | 18.09 |
| Perfluoroheptanesulfonate | PFHpS | 448.9334 | 20.30 |
| Perfluorooctanesulfonate | PFOS | 498.9302 | 21.75 |
| 6:2 chloro ether sulfonic acid | 6:2 Cl-PFESA | 530.8956 | 22.40 |
| 8:2 chloro ether sulfonic acid | 8:2 Cl-PFESA | 630.8892 | 24.07 |

(4) Non-target labeling of features of metabolites: the spectra obtained after instrumental analysis are converted into an ABF file, a backup file created by Analysis Services, a component of Microsoft SQL Server used for online analytical processing (OLAP) and data mining. The peaks in the ABF file are imported into MSDIAL software, a universal software program for untargeted metabolomics that supports multiple MS instruments and MS vendors, and aligned. Metabolites with detection rate greater than 80% and the peak area and mass spectrum corresponding to each peak are listed as a chromatographic peak table. Parameters are as follows:

peak picking mass range: 30-1250 Da;
peak picking mass error: 0.01 Da;
alignment retention time error: 0.5 min;
alignment mass error: 0.015 Da.

After 84 samples were analyzed, 3798 metabolites were finally labeled, and a sample metabolite matrix of 84×3798 was obtained.

(5) Non-target screening of biomarkers: a linear regression model is established in SPSS® software, a software package used for interactive, or batched, statistical analysis. the dependent variables are the peak areas of the features of the potential metabolites subjected to non-target labeling in (4), the independent variables are the peak areas of the features of the perfluorinated pollutants in (3) respectively, and the model with significance p<0.05 after model operation is regarded as an effective model. The number of biomarkers related to exposure of each perfluorinated compound can be obtained. Table 4 shows the number of biomarkers corresponding to nine perfluorinated compounds obtained in this step.

TABLE 4

Number of biomarkers corresponding to
the nine perfluorinated compounds

| Name | Abbreviation | Biomarker quantity |
|---|---|---|
| Perfluorooctanoate | PFOA | 1583 |
| Perfluorononanoate | PFNA | 506 |
| Perfluorodecanoate | PFDA | 664 |
| Perfluoroundecanoate | PFUnDA | 427 |
| Perfluorohexanesulfonate | PFHxS | 1639 |
| Perfluoroheptanesulfonate | PFHpS | 381 |
| Perfluorooctanesulfonate | PFOS | 140 |
| 6:2 chloro ether sulfonic acid | 6:2 Cl-PFESA | 53 |
| 8:2 chloro ether sulfonic acid | 8:2 Cl-PFESA | 76 |

(6) High-throughput identification of biomarkers: the MS spectra and MS/MS spectra of biomarkers obtained in step (5) are subjected to programmed identification by multi-platform combination. Firstly, MSP (a file extension associated with Windows Installer Patch file used for updating Windows and Microsoft programs) files in positive and negative ion modes are loaded in MSDIAL software, a universal software program for untargeted metabolomics that supports multiple MS instruments and MS vendors, respectively for metabolite library alignment. Unmatched metabolic characteristic peaks are uploaded to MetDNA platform, an internet-based platform with URL of http://metdna.zhulab.cn/ that implements a metabolic reaction network (MRN) based recursive algorithm for metabolite identification and supports data from different LC systems, and MS platforms for further identification. Identification results are classified in confidence level according to the standard recommended by Metabolites Standards Initiative (MSI): the metabolites identified by MSDIAL are at level 2; the "seed" metabolites identified by MetDNA are level 2, and other metabolites identified by MetDNA are at level 3, wherein MSDIAL is a universal software program for untargeted metabolomics that supports multiple MS instruments and MS vendors, and MetDNA platform is an internet-based platform with URL at http://metdna.zhulab.cn/ that implements a metabolic reaction network (MRN) based recursive algorithm for metabolite identification and supports data from different LC systems and MS platforms. MSDIAL parameters are as follows:

mass error: MS 0.01 Da, MS/MS 0.05 Da.
threshold of score: 80 points.

Table 5 shows the number of biomarkers corresponding to nine perfluorinated compounds identified in this step.

TABLE 5

Number of biomarkers corresponding to the
nine identified perfluorinated compounds

| Name | Abbreviation | Biomarker quantity |
|---|---|---|
| Perfluorooctanoate | PFOA | 235 |
| Perfluorononanoate | PFNA | 63 |
| Perfluorodecanoate | PFDA | 99 |
| Perfluoroundecanoate | PFUnDA | 60 |
| Perfluorohexanesulfonate | PFHxS | 243 |
| Perfluoroheptanesulfonate | PFHpS | 55 |
| Perfluorooctane sulfonate | PFOS | 17 |
| 6:2 chloro ether sulfonic acid | 6:2 Cl-PFESA | 9 |
| 8:2 chloro ether sulfonic acid | 8:2 Cl-PFESA | 21 |

(7) Correction of a biomarker non-target screening model: false positive results are reduced through multiple corrections, which are as follows, respectively:

false discovery rate (FDR) correction: R software is used to correct the threshold $p<0.05$ to FDR<20% through a qvalue command;

interference factor correction: interference factors (age, weight, residence) existing in samples are added to the regression model as covariates for correction; and co-exposure correction: when a model of a perfluorinated compound is analyzed, a multiple regression model is operated by taking biomarkers as dependent variables and 8 other perfluorinated compounds as independent variables, and a "stepwise" method is selected to retain significant perfluorinated compounds as independent variables and delete non-significant perfluorinated. After operation of the model, the regression model of the following three objects is obtained: 1) dependent variable: biomarker; 2) independent variable 1: the specific perfluorinated compound analyzed; (3) independent variable 2: significant perfluorinated compounds among 8 perfluorinated compounds. In this case, the significance of item 2) (independent variable 1: a perfluorinated compound analyzed) is the significance p value after correction, and the metabolite with the p value still less than 0.05 is used as the final biomarker corresponding to this perfluorinated compound. The high-throughput identification of biomarkers is implemented by step (6).

Table 6 shows the number of biomarkers corresponding to the nine identified perfluorinated compounds by using the corrected model.

TABLE 6

Number of identified biomarkers corresponding to the
nine perfluorinated compounds after correction

| Name | Abbreviation | Biomarker quantity |
|---|---|---|
| Perfluorooctanoate | PFOA | 64 |
| Perfluorononanoate | PFNA | 21 |

TABLE 6-continued

Number of identified biomarkers corresponding to the nine perfluorinated compounds after correction

| Name | Abbreviation | Biomarker quantity |
|---|---|---|
| Perfluorodecanoate | PFDA | 33 |
| Perfluoroundecanoate | PFUnDA | 14 |
| Perfluorohexanesulfonate | PFHxS | 147 |
| Perfluoroheptanesulfonate | PFHpS | 3 |
| Perfluorooctane sulfonate | PFOS | 0 |
| 6:2 chloro ether sulfonic acid | 6:2 Cl-PFESA | 1 |
| 8:2 chloro ether sulfonic acid | 8:2 Cl-PFESA | 1 |

(8) Metabolic pathway enrichment of the biomarkers: the biomarkers are enriched into metabolic pathways. The metabolic pathways disturbed by perfluorinated compounds include steroid hormone biosynthesis, arachidonic acid metabolism, α-linolenic acid metabolism, linoleic acid metabolism and retinol metabolism.

Comparative Example 1

The procedures of this comparative example are basically the same as those of Example 1, except that in step (7), only FDR correction and interference factor correction are adopted, and the model is not corrected by co-exposure correction. Table 7 shows the number of biomarkers corresponding to the nine perfluorinated compounds finally identified.

TABLE 7

Number of identified biomarkers corresponding to the nine perfluorinated compounds

| Name | Abbreviation | Biomarker quantity |
|---|---|---|
| Perfluorooctanoate | PFOA | 190 |
| Perfluorononanoate | PFNA | 27 |
| Perfluorodecanoate | PFDA | 48 |
| Perfluoroundecanoate | PFUnDA | 14 |
| Perfluorohexanesulfonate | PFHxS | 218 |
| Perfluoroheptanesulfonate | PFHpS | 3 |
| Perfluorooctane sulfonate | PFOS | 0 |
| 6:2 chloro ether sulfonic acid | 6:2 Cl-PFESA | 1 |
| 8:2 chloro ether sulfonic acid | 8:2 Cl-PFESA | 1 |

By comparison with the results obtained in Example 1, it can be seen that the model correction without co-exposure correction increases the false positive of the results to a certain extent.

Example 2

The procedures of this example are basically the same as those of Example 1, except that the step of docking perfluorooctanoate (PFOA) and perfluorooctane sulfonate (PFOS) which are the two most widely studied perfluorinated compounds is added before step (5) to predict their metabolic disturbance capabilities.

Molecules of PFOA and PFOS are subjected to structural optimization in the SYBYL® software, a molecular modeling program for creating molecular model from sequence through lead optimization and has capabilities for small molecule modeling and simulation, macromolecular modeling and simulation, and cheminformatics and lead identification. Tripos force field, Gasteiger-Huckel charge and a Powell gradient method are applied until the termination gradient drops below 0.001 kcal/(mol·Å).

Figure 5:
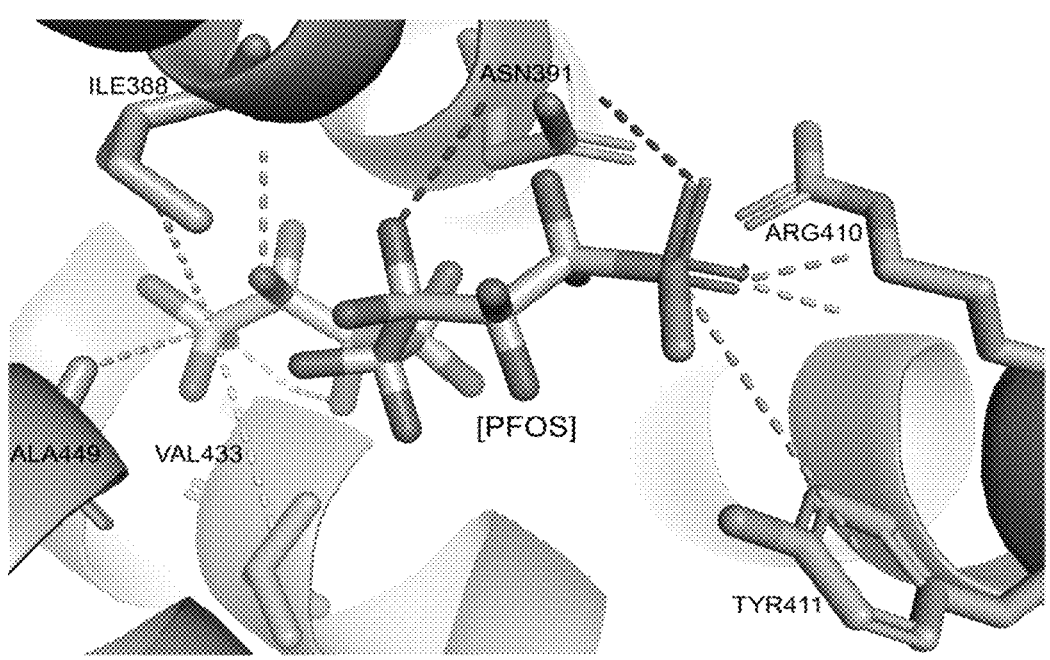
FIG. 5 shows the docking result of perfluorooctane sulfonate and human serum albumin in Example 2.

After the structure of human serum albumin is downloaded, the ligand is extracted from the SYBYL® software, a molecular modeling program for creating molecular model from sequence through lead optimization and has capabilities for small molecule modeling and simulation, macromolecular modeling and simulation, and cheminformatics and lead identification, to form a docking pocket, and the crystal water is removed and protonated. The optimized perfluorinated ligand and the protein pocket are docked in the SYBYL® software, a molecular modeling program for creating molecular model from sequence through lead optimization and has capabilities for small molecule modeling and simulation, macromolecular modeling and simulation, and cheminformatics and lead identification, and an optimum conformation is selected as docking result. When the total score of the docking result is greater, the docking ability is stronger, and free pollutants are less; otherwise, free pollutants are more, which may lead to stronger transient metabolic disorder and more biomarkers. The conformation obtained by docking is shown in FIG. 5. The docking results are shown in Table 8.

TABLE 8

Results of docking of the perfluorinated ligand and the protein pocket

| Name | Abbreviation | Total score | Kd |
|---|---|---|---|
| Perfluorooctanoate | PFOA | 3.9573 | $1.10 \times 10^{-4}$ |
| Perfluorooctane sulfonate | PFOS | 4.3431 | $4.54 \times 10^{-5}$ |

The results of subsequent biomarker screening of Example 1 show that PFOA indeed has stronger transient metabolic disturbance than PFOS. When a large number of pollutants are screened, using Example 2 can focus on pollutants with strong metabolic disturbance, which can reduce workload and improve efficiency.

What is claimed is:

1. A method for screening of non-target biomarkers based on a metabolic disturbance caused by pollutants, comprising the following steps:
    (1) performing sample treatment, and extracting pollutants and metabolites from biological samples to obtain extracts to be tested;
    (2) performing scan analysis and detection of the extracts to be tested through a high performance liquid chromatography—time-of-flight mass spectrometer to obtain a spectrum containing chromatographic peaks;
    (3) identifying and labeling features of pollutants according to the spectrum, taking chromatographic peaks other than the features of the pollutants as features of the potential metabolites, and performing non-target labeling of the features of the potential metabolites;
    (4) establishing a linear regression model by taking the peak areas of the features of the potential metabolites as dependent variables and the peak areas of the features of the pollutants as independent variables;
    (5) operating the model to perform non-target screening of the biomarkers, obtaining related biomarkers by preliminary screening; and
    (6) identifying the mass spectrometry (MS) spectra and Tandem mass spectrometry (MS/MS) spectra of the biomarkers obtained in step (5), and identifying biomarkers related to pollutant exposure.

2. The method for screening of non-target biomarkers based on a metabolic disturbance caused by pollutants according to claim 1, wherein the method further comprises step (7): using a correction method to correct the model, operating the corrected model, and repeating steps (5)-(6).

3. The method for screening of non-target biomarkers based on a metabolic disturbance caused by pollutants according to claim 2, wherein the correction method comprises false discovery rate (FDR) correction and interference factor correction; in the process of the FDR correction, threshold $p<0.05$ is corrected to be FDR<20%; and in the process of the interference factor correction, interference factors existing in samples are added to the model as covariates for correction.

4. The method for screening of non-target biomarkers based on a metabolic disturbance caused by pollutants according to claim 2, wherein when the extracts to-be-tested contain multiple pollutants, the correction method comprises a co-exposure correction method comprised of taking multiple pollutants as potential independent variables to perform multiple stepwise regression and model correction.

5. The method for screening of non-target biomarkers based on a metabolic disturbance caused by pollutants according to claim 4, wherein in the process of identifying the features of the pollutants, the spectrum is converted into a data file, and the peaks in the data file are imported into a Mass Spec data interrogation software and aligned for analysis to identify the pollutants.

6. The method for screening of non-target biomarkers based on a metabolic disturbance caused by pollutants according to claim 5, wherein in the process of non-target labeling of the features of the potential metabolites, the spectrum is converted into a backup file, the peaks in the backup file are imported into a software program for untargeted metabolomics and aligned, and the features with detection rate greater than 80% are retained as the features of the potential metabolites.

7. The method for screening of non-target biomarkers based on a metabolic disturbance caused by pollutants according to claim 4, wherein in step (4), the model with significance $p<0.05$ after operation is taken as an effective model to implement the operation process of step (5).

8. The method for screening of non-target biomarkers based on a metabolic disturbance caused by pollutants according to claim 7, wherein in step (6), a software program for untargeted metabolomics and an internet-based metabolite identification platform are combined to identify the biomarkers.

9. The method for screening of non-target biomarkers based on a metabolic disturbance caused by pollutants according to claim 8, wherein in step (2), the adopted detection conditions are as follows:

high performance liquid chromatographic instrument: Infinity1260;

chromatographic column: C18 column: 2.1 mm×50 mm, 2.5 μm;

column temperature: 40° C.;

flow rate: 0.4 mL/min;

mobile phase: phase A in positive ion mode: 0.1% formic acid-aqueous solution; phase A in negative ion mode: 2 mM ammonium acetate aqueous solution; and phase B: methanol;

the gradient elution conditions are as follows:

| Time (min) | A % | B % |
| --- | --- | --- |
| 1.00 | 95 | 5 |
| 11.00 | 75 | 25 |
| 19.00 | 50 | 50 |
| 25.00 | 25 | 75 |
| 29.00 | 0 | 100 |
| 32.00 | 0 | 100 |
| 32.01 | 95 | 5 |
| 36.00 | 100 | 0 | full scan mode: data dependence mode;

ion source: positive and negative electrospray ionization source;

full scan mass range: MS 50-1250 Da, MS/MS 30-1000 Da;

collision energy: ±40 eV;

collision energy spread: 20 eV;

ion source temperature: 550° C.

10. The method for screening of non-target biomarkers based on a metabolic disturbance caused by pollutants according to claim 2, wherein the method further comprises the step of metabolic pathway enrichment of the biomarkers, and in this step, the identified biomarkers are enriched into metabolic pathways to obtain metabolic pathways disturbed by pollutants.

11. The method for screening of non-target biomarkers based on a metabolic disturbance caused by pollutants according to claim 1, wherein the method further comprises the step of metabolic pathway enrichment of the biomarkers, and in this step, the identified biomarkers are enriched into metabolic pathways to obtain metabolic pathways disturbed by pollutants.

* * * * *